United States Patent [19]
Stone et al.

[11] Patent Number: 5,578,036
[45] Date of Patent: Nov. 26, 1996

[54] METHOD AND APPARATUS FOR FIXATION OF BONE DURING SURGICAL PROCEDURES

[76] Inventors: Kevin T. Stone, 2940 E. Patterson Rd., Warsaw, India. 46580; Stephen J. Foss, 10841 Brooks La., Plymouth, Mich. 48170

[21] Appl. No.: 163,334

[22] Filed: Dec. 6, 1993

[51] Int. Cl.⁶ ............................... A61B 17/56; A61F 2/30
[52] U.S. Cl. ............................................................. 606/69
[58] Field of Search ................................ 606/56, 69, 70, 606/71, 96, 97, 98, 101, 102, 104; 411/457, 461, 469

[56] References Cited

U.S. PATENT DOCUMENTS

| | | |
|---|---|---|
| 2,238,238 | 4/1941 | Westrope . |
| 2,329,471 | 9/1943 | King . |
| 2,791,868 | 5/1957 | Viken . |
| 2,846,744 | 8/1958 | Becker . |
| 4,116,200 | 9/1978 | Braun et al. . |
| 4,793,335 | 12/1988 | Frey et al. . |
| 5,201,737 | 4/1993 | Leibinger et al. ................... 606/69 |

FOREIGN PATENT DOCUMENTS

290138A2  11/1988  European Pat. Off. .

OTHER PUBLICATIONS

Internal Fixation of Small Fractures Technique Recommended by the AO–ASIF Group, U. Heim and K. M. Pfeiffer, ©Springer–Verlag Berlin Heidelberg 1974, 1982 and 1988.

Manual of Internal Fixation Technique Recommended by the AO–Group, M. E. Müller, M. Allgöwer, and H. Willenegger, ©Springer–Verlag, Berlin–Heidelberg 1970.

Brochure entitled "Neurosurgical Quality Instruments," Codman & Shurtleff, 1965, pp. 10–13.

*Primary Examiner*—Randy C. Shay
*Attorney, Agent, or Firm*—Harness, Dickey & Pierce, P.L.C.

[57] ABSTRACT

An apparatus for fixation of bone during surgical procedures using a bone screw. The apparatus includes a body member which is able to cover at least a portion of the bone. The apparatus also includes an attachment member which is able to be secured to the bone and is able to receive the bone screw. The apparatus also includes an extension member which is connected to the body member and the attachment member.

24 Claims, 3 Drawing Sheets

METHOD AND APPARATUS FOR FIXATION OF BONE DURING SURGICAL PROCEDURES

BACKGROUND OF THE INVENTION

1. Field of the Invention

This invention relates to prosthetic implant devices which are used in surgical procedures, and more particularly to a method and apparatus for fixation of bone during surgical procedures.

2. Description of the Related Art

During various types of surgical procedures, it is often necessary to remove and reattach a portion of bone such as a human skull. In certain neurosurgical procedures, for example, a cranial bone flap is first formed on the skull and then removed so that a surgeon can access the portions of the brain that are of concern. Such a cranial bone flap may typically be formed by drilling several burr holes through the cranial vault. After the burr holes have been drilled, osteotomies are made by a saw in the skull which connect the burr holes. The saw may typically have a guide nose which serves to avoid injuries to the dura mater. The bone flap is then removed so as to provide access to the brain. Once the procedures which are performed on the brain have been completed, the bone flap is reattached to the skull.

In craniofacial procedures, a bone segment is first formed on the skull in a manner similar to that described above and then the bone segment is removed from the skull. The bone segment is then shaped by the surgeon so as to provide the desired cosmetic appearance. Once the bone segment has been shaped in the desired manner, the bone segment is then reattached to the skull.

A variety of devices are commercially available which are used for securing a bone flap or a bone segment to the skull. For example, U.S. Pat. No. 5,210,737 discloses a device having a plurality of slots which extend radially from the center of the device. The slots are indicated as being used for forming a plurality of vanes in the device. This device, however, does not provide a high degree of flexibility with respect to placement of the bone screws which are used to secure the device to both the skull and the bone flap. Rather, the placement of the bone screws with respect to the body of the device is fixed and is determined by the specific geometry of the device. In addition, the slots which are located between the vanes of this device tend to limit the rigidity of the device. Finally, altering one or more of the vanes tends to deform the shape of the device which may cause interference at the interface between the device and both the skull and the bone flap.

SUMMARY OF THE INVENTION

In one embodiment, the present invention relates to an apparatus for fixation of bone during surgical procedures. The apparatus includes a body member which is operable to cover at least a portion of the bone. The apparatus also includes at least one attachment member which is operable to be secured to the bone. The attachment member includes means for receiving a bone screw and is operable to be secured to the bone upon receipt of the bone screw. The apparatus further includes an extension member that mechanically communicates with the body member and the attachment member and is operable to be displaced with respect to the body member. Because the extension member is displaceable with respect to the body member, the attachment member may be secured to the bone by the bone screw at a plurality of different positions with respect to the body member by varying the displacement of the extension member with respect to the body member.

In another embodiment, the present invention also relates to a method for covering a portion of a bone. The method includes the initial step of forming a body member which is operable to cover a portion of the bone, at least one attachment member which is operable to be secured to the bone, as well as an extension member mechanically communicating with the body member and the attachment member. The method also includes the step of determining the desired position of the body member as well as the bone screw with respect to the bone. The method also includes displacing the extension member with respect to the body member and then securing the apparatus to the bone by causing the bone screw to engage the attachment member and the bone.

Accordingly, an advantage of the present invention is to provide a method and apparatus for fixation of bone during surgical procedures which is relatively simple to use and which is adaptable to a variety of patients as well as a variety of surgical procedures and situations.

A further advantage of the present invention is to provide a method and apparatus for fixation of bone during surgical procedures in which the location of bone screws which attach the apparatus to bone may be varied.

Another advantage of the present invention is to provide a method and apparatus for fixation of bone during surgical procedures which is relatively strong yet is able to provide a relatively high degree of flexibility to the surgeon during fixation of the bone.

Another advantage of the present invention is to provide a method and apparatus for fixation of bone during surgical procedures in which the flow of fluid through the apparatus is relatively unimpeded yet is able to provide a relatively high degree of strength.

A further advantage of the present invention is to provide a method and apparatus for fixation of bone during surgical procedures which is expandable to accommodate the growth of the patient.

Another object of the present invention is to provide a method and apparatus for fixation of bone during surgical procedures which is relatively simple and which is easy to fabricate.

BRIEF DESCRIPTION OF THE DRAWINGS

Various advantages of the present invention will become apparent to one skilled in the art upon reading the following specification and reference to the following drawings in which.

DISCUSSION OF THE PREFERRED EMBODIMENTS

The following discussion of the preferred embodiments of the present invention is merely exemplary in nature. Accordingly, the discussion is in no way intended to limit the scope of the invention, the application of the invention, or the use of the invention.

Figure 1:
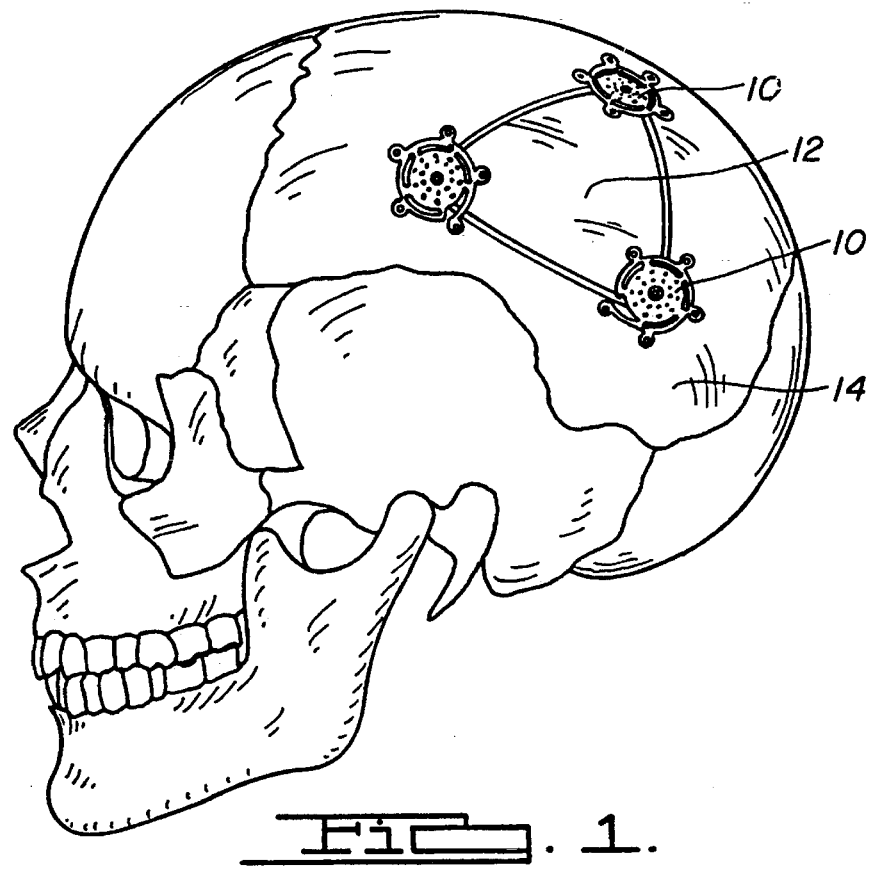
FIG. 1 is a view of the apparatus for fixation of bone during surgical procedures shown in operative association with a cranial bone flap and a human skull.

Referring to FIG. 1, an apparatus 10 for fixation of bone during surgical procedures is shown. The apparatus may be used for reattaching a cranial bone flap 12 to a skull 14 after the cranial bone flap 12 has been removed and various surgical procedures have been performed. In particular, the apparatus 10 may be used to cover a burr hole (not shown) which is formed during the creation of the cranial bone flap 12. As will be appreciated by those skilled in the art, the apparatus 10 may be used in a variety of neurosurgical and/or craniofacial procedures. In addition, the apparatus 10 may be used with other types of procedures where it is desirable to fixate bone, bone segments or other suitable forms of biological material.

Figure 2:
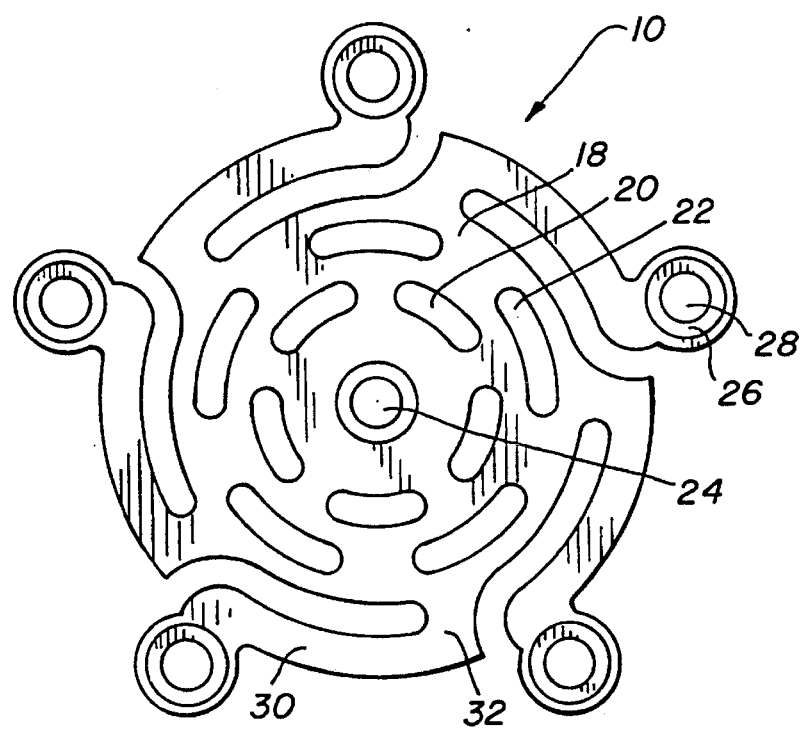
FIG. 2 is an enlarged front elevational view of the apparatus for fixation of bone during surgical procedures shown in FIG. 1 according to the first preferred embodiment of the present invention.
Figure 3:
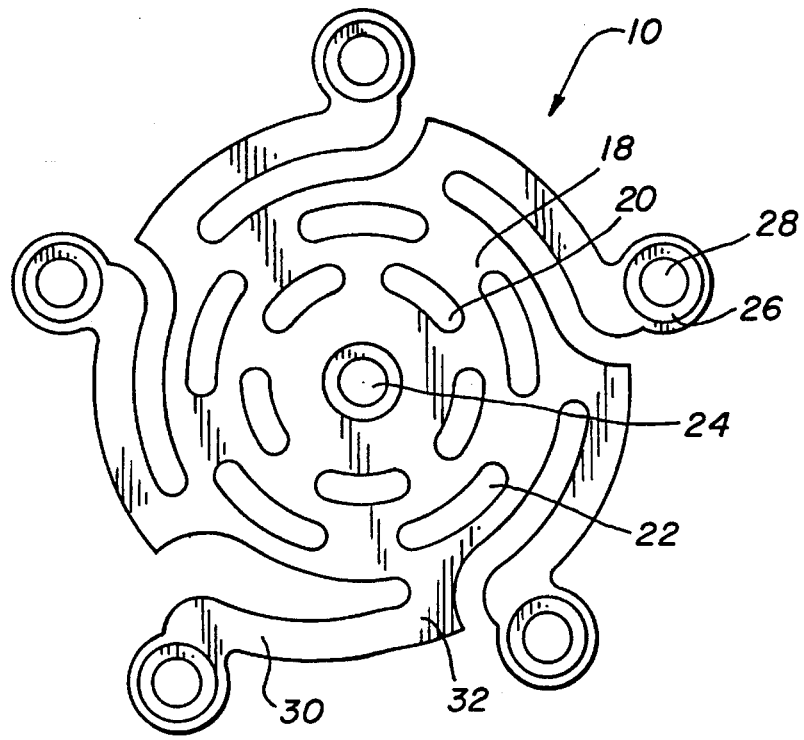
FIG. 3 is an enlarged front elevational view of the apparatus for fixation of bone during surgical procedures according to the first preferred embodiment of the present invention shown in FIG. 2 with one of the extension members being displaced.

The apparatus 10 according to the first preferred embodiment will now be described in further detail with reference to FIGS. 2 and 3. The apparatus 10 includes a body member 18 which is operable to cover at least a portion of a bone which may be the cranial bone flap 12, the skull 14, a burr hole, or any other suitable biological material. The body member 18 is substantially circular in configuration in that it is at least partially defined by a center and a radial centerline rotated about the center. The body member 18 may be convexly curved to generally correspond to the shape of the skull 14. In this case, it is preferable that the shape of the body member be formed by an arc with a radius of approximately 3 inches. While the body member 18 is preferably made from commercially pure titanium, it will be understood that any other suitable material may be used which is body compatible. Such materials include titanium alloys, chromium-cobalt-molybdenum alloys or other suitable materials.

To provide a plurality of flow passages through the body member 18 for fluid flowing proximate to the bone, the body member 18 further includes a first plurality of elongated apertures 20 and a second plurality of elongated apertures 22. The first plurality of elongated apertures 20 are arranged generally concentric with respect to the body member 18 in a region adjacent to the center of the body member 18. The second plurality of elongated apertures 22 are also arranged generally concentric with respect to the body member 18 though at a further distance from the center of the body member 18 than the first plurality of elongated apertures 20. Disposed centrally within the body member 18 is a central aperture 24 which also provides a path for fluids to flow through the apparatus 10 as well as provides an additional location for receiving a bone screw.

To provide means for securing the apparatus 10 to the bone, the apparatus 10 further includes a plurality of attachment members 26. The attachment members 26 extend radially from the outer periphery of the body member 18 and include a bone screw hole 28. The bone screw hole 28 is used to provide means for receiving a suitable bone screw (not shown). The bone screw hole 28 is located centrally on the attachment members 26 and serves to secure the attachment members 26 to the bone upon receipt of the bone screw.

To provide means for securing the attachment members 26 at a plurality of different positions with respect to the body member 18, the apparatus 10 further includes a plurality of extension members 30. The extension members 30 are disposed generally concentric with respect to the body member 18 and initially extend in the direction generally perpendicular with respect to the radial centerline of the body member 18. The extension members 30 also are integrally formed with the body member 18 and mechanically communicate with the attachment members 26. In this regard, the body member 18 includes a plurality of hinge portions 32 which are able to be deformed upon movement of the extension members 30 with respect to the body member 18 as shown in FIG. 3. Accordingly, each of the attachment members 26 may be located at a variety of positions with respect to the body member 18 upon movement of the corresponding extension member 30 and deformation of the hinge portion 32.

Because the attachment members 26 may be located at a variety of positions with respect to the body member 18, the attachment members 26 can be suitably located on the bone so as to provide optimum positioning of the body member 18 with respect to the bone while also providing optimum positioning of the bone screws. The apparatus 10 may therefore be configured to the specific needs of each particular application. In addition, because the extension members 30 may be displaced from the body member 18, the apparatus 10 is able to accommodate for the growth of the patient. In this regard, as the patient grows, the skull enlarges which causes further displacement of the extension members 30 from the body member 18.

The method of using the present invention will now be described as used in neurosurgical and craniofacial procedures. It is to be understood, however, that the apparatus 10 may be used with other procedures as well. The apparatus 10 is first formed having the body member 18, at least one attachment member 26, as well as an extension member 30. After the apparatus 10 has been formed, the bone flap 12 is then prepared by drilling several burr holes through the cranial vault. After the burr holes have been drilled, osteotomies are made in the skull which connects the burr holes. The saw which is used to form the osteotomies may preferably have a nose guide which serves to avoid injuries to the dura mater. The bone flap 12 is then removed so as to provide access to the brain or to allow the surgeon to shape the bone flap.

After the procedures on the brain have been completed or the bone flap 12 has been shaped, the bone flap 12 is replaced in the skull 14 to cover the defect. The apparatus 10 is then centrally located over one of the burr holes. The surgeon then determines the desired position of the body member 18 with respect to the bone, as well as determines the desired position for the bone screws which will be used to secure the apparatus 10 to the bone. Several or all of the extension members 30 of the apparatus 10 may then be displaced from the body member 18 so as to provide the desired positioning of the attachment members 26 with respect to both the bone flap 12 and the skull 14. Suitable holes are then drilled in the bone flap 12 and the skull 14.

Bone screws are then inserted through the holes in the attachment members 26 and into the holes in the bone flap 12 and the skull 14. It will be appreciated that the apparatus 10 does not require each of the attachment members 26 to receive a bone screw. Rather, the surgeon can select which of the attachment members 26 are to receive a bone screw to positionally secure the apparatus 10 to both the bone flap 12 as well as the skull 14. However, it will be understood that it is generally preferable to fill each of the holes in the attachment members 26 with bone screws.

Figure 4:
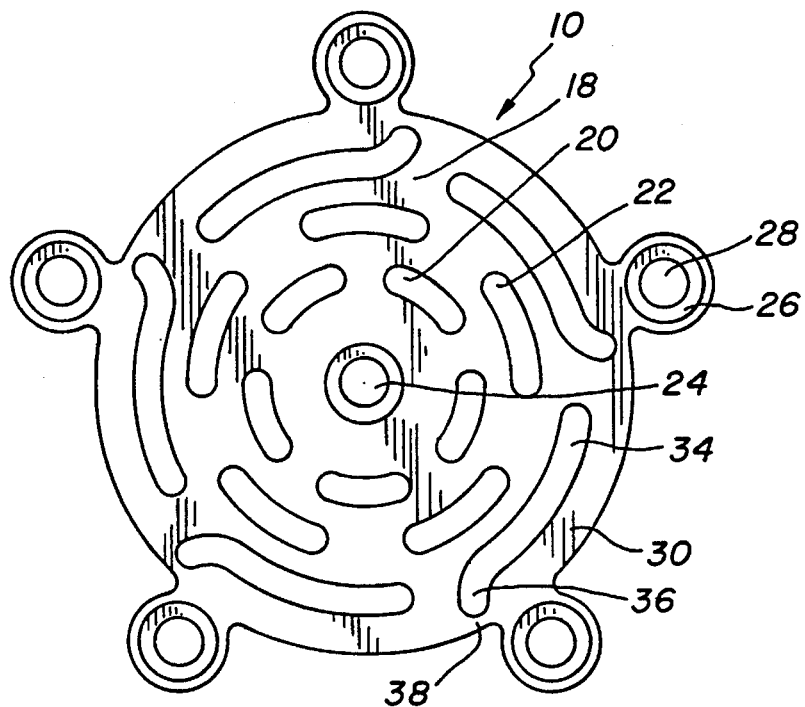
FIG. 4 is an enlarged front elevational view of the apparatus for fixation of bone during surgical procedures shown in FIG. 1 according to the second preferred embodiment of the present invention.

The second preferred embodiment of the present invention will now be described with reference to FIG. 4. In this regard, like reference numerals will be used to identify similar structures as described with respect to the first preferred embodiment of the present invention. The apparatus 10 according to the second preferred embodiment of the present invention further includes a third plurality of elongated apertures 34. The third plurality of elongated apertures 34 are disposed generally concentric with respect to the body member 18, though at a distance further from the center of the body member 18 than the second plurality of elongated apertures 22. Each of the elongated apertures 34 includes a curved end portion 36 which is disposed at a distance which is closer to the outer periphery of the body member 18 than the remaining portion of the elongated apertures 34.

The portion of the body member 18 between the curved end portion 36 of the elongated apertures 34 and the outer periphery of the body member 18 is operable to form a latch portion 38. The latch portion 38 of the body member 18 serves to secure the extension member 30 to the body member 18 until it is desirable to displace the extension member 30 with respect to the body member 18. When it becomes desirable to displace the extension member 30 in this manner, the latch portion 38 of the body member 18 is severed so as to permit the extension member 30 to be moved with respect to the body member 18. Accordingly, the latch portion 38 provides additional support to the attachment member 26 when the latch portion 38 is not severed, yet permits the extension member 30 to be displaced so as to allow the attachment member 26 to be placed at a variety of locations when necessary by severing the latch portion 38. As will be appreciated by those skilled in the art, the method of using the apparatus 10 according to this preferred embodiment of the present invention is similar to that described above.

Figure 5:
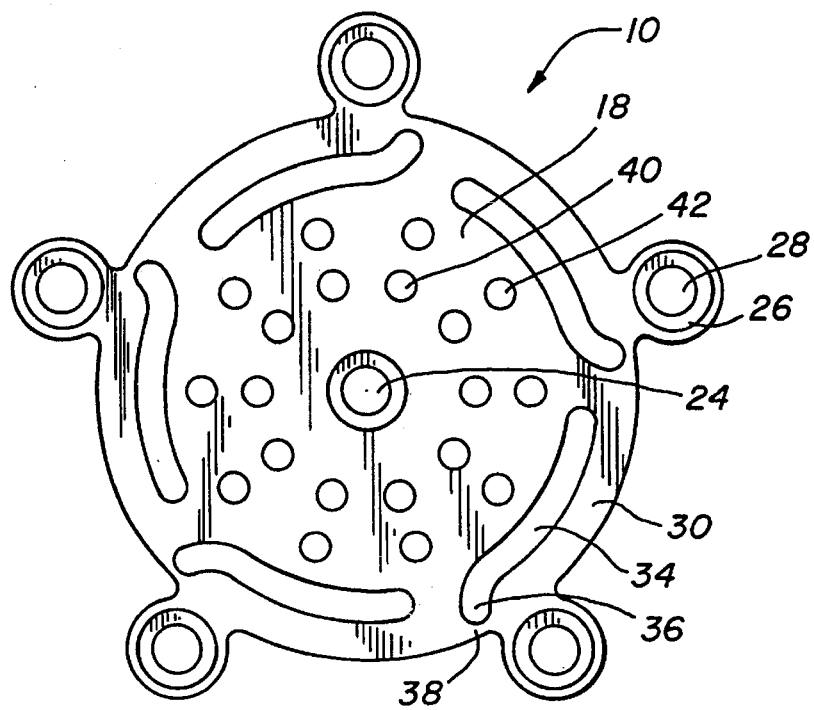
FIG. 5 is an enlarged front elevational view of the apparatus for fixation of bone during surgical procedures shown in FIG. 1 according to the third preferred embodiment of the present invention.

The third preferred embodiment of the present invention will now be described with reference to FIG. 5. In this regard, like numerals are used to identify similar elements as described with respect to the second preferred embodiment of the present invention. The apparatus 10 according to the third preferred embodiment of the present invention functions in a manner similar to that described with respect to the second preferred embodiment of the present invention. However, the third preferred embodiment does not include the first plurality of elongated apertures 20 as well as the second plurality of elongated apertures 22. Rather, the third preferred embodiment of the present invention includes a first plurality of circular apertures 40 as well as a second plurality of circular apertures 42. The first and second plurality of circular apertures 40 and 42 serve to provide for the flow of fluids through the apparatus 10. The first plurality of circular apertures 40 are concentrically disposed with respect to the body member 18 at a position relatively close to the center of the body member 18. The second plurality of circular apertures 42 are also concentrically disposed with respect to the body member 18 at a position between the first plurality of circular apertures 40 and the elongated apertures 34. As will be appreciated by those skilled in the art, the method of using the apparatus 10 according to this preferred embodiment of the present invention is similar to that described above.

Figure 6:
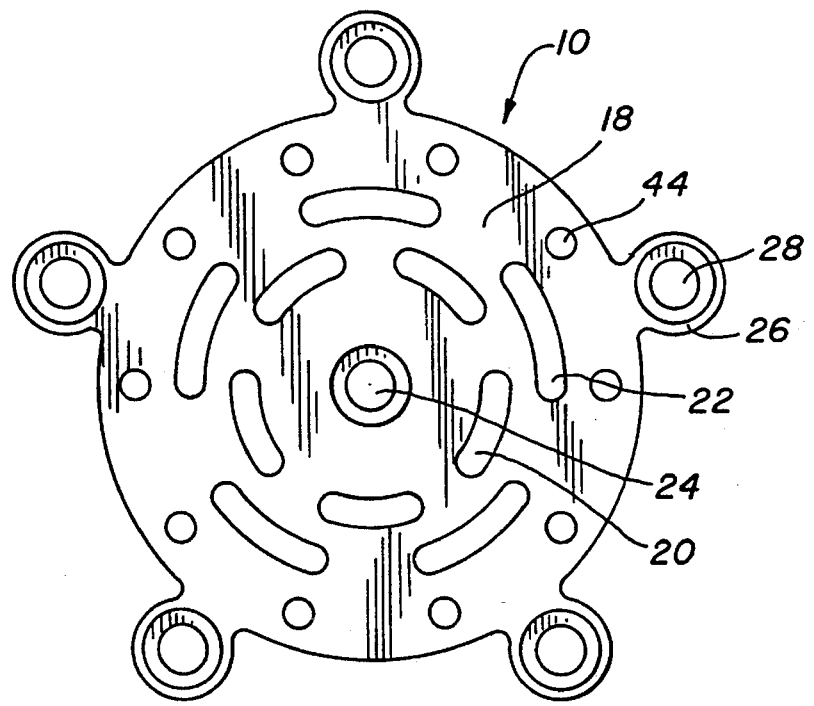
FIG. 6 is an enlarged front elevational view of the apparatus for fixation of bone during surgical procedures shown in FIG. 1 according to the fourth preferred embodiment of the present invention.

The fourth preferred embodiment of the present invention will now be described with reference to FIG. 6. In this regard, like reference numerals will be used to identify similar features as described with respect to the second preferred embodiment of the present invention. The apparatus 10 according to the fourth preferred embodiment of the present invention does not include the third plurality of elongated apertures 34. Rather, the third preferred embodiment of the present invention includes a plurality of circular apertures 44. The plurality of circular apertures 44 are concentrically disposed with respect to the body member 18 and are disposed between the second plurality of elongated apertures 22 and the attachment members 26. The plurality of circular apertures 44 serve to facilitate the flow of fluid through the apparatus 10. As will be appreciated by those skilled in the art, the method of using the apparatus 10 according to this preferred embodiment of the present invention is similar to that described above. However, it will be understood that the apparatus 10 according to this embodiment does not have extension members which serves to allow the attachment members 26 to be oriented at a variety of positions with respect to the body member 18.

Those skilled in the art can now appreciate from the foregoing that the broad teachings of the present invention can be implemented in a variety of forms. Therefore, while the invention was described in connection with particular examples hereof, the true scope of the invention should not be so limited. For example, the present invention may be used with a variety of surgical procedures which may not necessarily involve neurosurgical and/or craniofacial procedures. In addition, the body member does not necessarily have to be substantially circular in configuration but may be of other shapes which are desirable for a particular application. While there are preferably five attachment members associated with each embodiment of the present invention, it will be understood that either greater or fewer attachment members may be present. In addition, the extension members may be of other suitable shapes and sizes which are desirable for a given application. Other modifications will become apparent to those skilled in the art.

What is claimed is:

1. An apparatus for fixation of bone during surgical procedures using at least one bone screw, said apparatus comprising:

a body member defining a plane which is operable to cover at least a portion of the bone;

at least one attachment member which is operable to be secured to the bone, said at least one attachment member including means for receiving the at least one bone screw and securing said at least one attachment member to the bone upon receipt of the at least one bone screw; and at least one extension member mechanically communicating with said body member and a respective one of said at least one attachment member, a distal end of said at least one extension member being operable to be displaced generally radially with respect to said body member within the plane of the body member whereby by varying the displacement of said extension member with respect to said body member, said at least one attachment member may be secured to the bone by the at least one bone screw at a plurality of different positions with respect to said body member.

2. The apparatus as set forth in claim 1, wherein the bone includes a burr hole, said body member, said at least one attachment member, and said at least one extension member are operable to form a burr hole cover.

3. The apparatus as set forth in claim 1, wherein said body member includes a hinge portion which is operable to allow said extension member to be displaced with respect to said body member.

4. The apparatus as set forth in claim 1, wherein said body member includes a latch portion which is operable to selectively allow said extension member to be displaced with respect to said body member.

5. The apparatus as set forth in claim 1, wherein said body member is substantially circular in configuration and being at least partially defined by a center and a radial centerline rotated about said center, said extension member being operable to extend in a direction generally perpendicular with respect to said radial centerline of said body member.

6. The apparatus as set forth in claim 1, wherein said body member further includes a plurality of elongated apertures, said elongated apertures being arranged generally concentrically with respect to said body member.

7. The apparatus as set forth in claim 6, wherein said body member further includes a plurality of generally circular apertures, said plurality of generally circular apertures being arranged generally concentrically with respect to said body member.

8. The apparatus as set forth in claim 1, wherein said extension member is integrally formed with said body member.

9. A method for fixating bone during surgical procedures using a bone screw, said method comprising the steps of:

forming an apparatus for fixation of the bone, said apparatus including:
(a) a body member defining a plane which is operable to cover at least a portion of the bone,
(b) at least one attachment member which is operable to be secured to the bone, said at least one attachment member including means for receiving the bone screw and securing said at least one attachment member to the bone upon receipt of the bone screw, and
(c) at least one extension member mechanically communicating with a respective one of said body member and said at least one attachment member, a distal end of said at least one extension member being operable to be displaced generally radially with respect to said body member within the plane of the body member determining a desired position of said body member with respect to the bone;

determining a desired position of the bone screw with respect to the bone;

displacing said extension member with respect to said body member in response to said step of determining the desired position of said body member and said step of determining the desired position of the bone screw; and securing said apparatus to the bone by causing the bone screw to engage said at least one attachment member and the bone.

10. The method for fixating bone during surgical procedures according to claim 9, wherein said body member further comprises a hinge portion mechanically communicating with said extension member, said step of displacing said extension member including the step of deforming said hinge portion.

11. The method for fixating bone during surgical procedures as set forth in claim 9, wherein said body member further comprises a plurality of extension members which are operable to be secured to the bone using a plurality of bone screws, said method further comprising the additional steps of:
(a) displacing said plurality of extension members with respect to said body member in response to said step of determining the desired position of said bone screws, and
(b) securing said plurality of extension members to said bone using said plurality of bone screws.

12. The method for fixating bone during surgical procedures as set forth in claim 9, wherein said step of forming an apparatus for fixation of the bone further comprises the additional step of forming a plurality of concentrically disposed elongated flow passages in said body member.

13. The method for fixating bone during surgical procedures as set forth in claim 9, wherein said step of forming an apparatus for fixation of the bone further comprises the step of forming a latch portion between said extension member and said body member.

14. The method for fixating bone during surgical procedures as set forth in claim 13, further comprising the additional step of determining whether to sever said latch portion is in response to said step of determining the desired position of said body member and said step of determining the desired position of the bone screw.

15. An apparatus for fixation of bone during surgical procedures which is operable to cover a burr hole formed in said bone, said apparatus being further operable to be secured to said bone using a plurality of bone screws, said apparatus comprising:

a body member which is operable to cover said burr hole;

a plurality of attachment members extending radially from said body member which are operable to be secured to the bone, each of said attachment members including means for receiving one of the bone screws so as to secure said attachment members to said bone;

a plurality of latch portions which mechanically communicate with said extension members, said latch portions being operable to selectively allow said extension members to be displaced with respect to said body member; and a plurality of elongated flow passages disposed on said body member, said plurality of elongated flow passages being disposed concentrically with respect to the center of said body member, whereby said body member is operable to be secured to the bone in a position covering said burr hole and fluid flowing proximate to the bone is operable to flow through said body member.

16. The apparatus for fixation of bone during surgical procedures as set forth in claim 15, further comprising a plurality of circular flow passages which are disposed on said body member concentrically with said plurality of elongated flow passages.

17. The apparatus for fixation of bone during surgical procedures as set forth in claim 15, further comprising a plurality of extension members, each of said extension members being disposed between each of said attachment members and said body member, each of said extension members being operable to be displaced with respect to said body member.

18. The apparatus for fixation of bone during surgical procedures as set forth in claim 17, wherein said body member further comprises a plurality of hinge portions which mechanically communicate with said extension members, said hinge portions permitting said extension members to be displaced with respect to said body member.

19. The apparatus for fixation of bone during surgical procedures as set forth in claim 18, wherein said body member is substantially circular in configuration.

20. The apparatus for fixation of bone during surgical procedures as set forth in claim 19, wherein said body member is convexly curved.

21. An apparatus for fixation of bone during surgical procedures using at least one bone screw, said apparatus comprising:

a body member defining a generally planar surface which is operable to cover at least a portion of the bone;

at least one attachment member which is operable to be secured to the bone, the at least one attachment member including means for receiving the at least one bone screw and securing said at least one attachment member to the bone upon receipt of the at least one bone screw; and at least one extension member mechanically communicating with said body member and a respective one of said at least one attachment member, a distal end of said at least one extension member being operable to be displaced generally radially with respect to said body member within the plane of the body member, said body member including a latch portion which is operable to selectively allow said extension member to be displaced with respect to said body member, whereby by varying the displacement of said extension member with respect to said body member, said at least one attachment member may be secured to the bone by the at least one bone screw at a plurality of different positions with respect to said body member.

22. An apparatus for fixation of bone during surgical procedures using at least one bone screw, said apparatus comprising:

a body member which is operable to cover at least a portion of the bone;

at least one attachment member which is operable to be secured to the bone, said at least one attachment member including means for receiving the at least one bone screw and securing said at least one attachment member to the bone upon receipt of the at least one bone screw; and at least one extension member mechanically communicating with said body member and a respective one of said at least one attachment member, said at least one extension member being operable to be positioned with respect to said body member, said body member being substantially circular in configuration and being at least partially defined by a center and a radial centerline rotated about said center, said at least one extension member being operable to extend in a direction generally perpendicular with respect to said radial centerline of said body member;

whereby by varying the position of said at least one extension member with respect to said body member, said at least one attachment member may be secured to the bone by the at least one bone screw at a plurality of different positions with respect to said body member by varying the position of said at least one extension member with respect to said body member.

23. A method for fixating bone during surgical procedures using a bone screw, said method comprising the steps of:

forming an apparatus for fixation of the bone, said apparatus including:
 (a) a body member defining a generally planar surface which is operable to cover at least a portion of the bone,
 (b) at least one attachment member which is operable to be secured to the bone, said at least one attachment member including means for receiving the bone screw and securing said at least one attachment member to the bone upon receipt of the bone screw,
 (c) at least one extension member mechanically communicating with a respective one of said body member and said at least one attachment member, a distal end of said at least one extension member being operable to be displaced generally radially with respect to said body member within the plane of the body member, and
 (d) a latch portion situated between said extension member and said body member;

determining a desired position of said body member with respect to the bone;

determining a desired position of the bone screw with respect to the bone;

displacing said extension member with respect to said body member in response to said step of determining the desired position of said body member and said step of determining the desired position of the bone screw; and securing said apparatus to the bone by causing the bone screw to engage said at least one attachment member and the bone.

24. An apparatus for fixation of bone during surgical procedures which is operable to cover a burr hole formed in the bone, said apparatus being further operable to be secured to the bone using a plurality of bone screws, said apparatus comprising:

a body member which is operable to cover the burr hole;

a plurality of attachment members extending radially from said body member that are operable to be secured to the bone, each of said attachment members including means for receiving one of the bone screws so as to secure said attachment members to the bone;

a plurality of elongated flow passages disposed on said body member, said plurality of elongated flow passages being disposed concentrically with respect to the center of said body member; and a plurality of extension members, each of said extension members being disposed between a respective one of said attachment members and said body member, each of said extension members being operable to be moved with respect to said body member, said body member further comprises a plurality of latch portions which mechanically communicate with said extension members, said latch portions being operable to selectively allow said extension members to be moved with respect to said body member;

whereby said body member is operable to be secured to the bone in a position covering the burr hole and fluid flowing proximate to the bone is operable to flow through said body member.

* * * * *

UNITED STATES PATENT AND TRADEMARK OFFICE
CERTIFICATE OF CORRECTION

PATENT NO. : 5,578,036
DATED : November 26, 1996
INVENTOR(S) : Kevin T. Stone, et al It is certified that error appears in the above-identified patent and that said Letters Patent is hereby corrected as shown below:

Column 7, line 19, claim 9, after "member", insert--;--

Signed and Sealed this

Fifth Day of May, 1998

Attest:

BRUCE LEHMAN

Attesting Officer

Commissioner of Patents and Trademarks